United States Patent
Nosaka et al.

(10) Patent No.: US 11,454,890 B2
(45) Date of Patent: Sep. 27, 2022

(54) COMPOSITION FOR RESIST UNDERLAYER FILM FORMATION, RESIST UNDERLAYER FILM AND FORMING METHOD THEREOF, PATTERNED SUBSTRATE-PRODUCING METHOD, AND COMPOUND

(71) Applicant: JSR CORPORATION, Tokyo (JP)

(72) Inventors: Naoya Nosaka, Tokyo (JP); Yuushi Matsumura, Tokyo (JP); Hiroki Nakatsu, Tokyo (JP); Kazunori Takanashi, Tokyo (JP); Hiroki Nakagawa, Tokyo (JP)

(73) Assignee: JSR CORPORATION, Tokyo (JP)

( * ) Notice: Subject to any disclaimer, the term of this patent is extended or adjusted under 35 U.S.C. 154(b) by 236 days.

(21) Appl. No.: 16/871,131

(22) Filed: May 11, 2020

(65) Prior Publication Data

US 2020/0272053 A1 Aug. 27, 2020

Related U.S. Application Data (63) Continuation of application No. PCT/JP2018/041410, filed on Nov. 7, 2018.

(30) Foreign Application Priority Data

Nov. 16, 2017 (JP) .............. JP2017-221341

(51) Int. Cl.
| | | |
|---|---|---|
| G03F 7/11 | (2006.01) | |
| C09D 7/63 | (2018.01) | |
| C07D 241/24 | (2006.01) | |
| H01L 21/027 | (2006.01) | |
| C07D 251/24 | (2006.01) | |
| G03F 7/16 | (2006.01) | |
| G03F 7/20 | (2006.01) | |
| G03F 7/30 | (2006.01) | |

(52) U.S. Cl.
CPC .............. *G03F 7/11* (2013.01); *C07D 251/24* (2013.01); *C09D 7/63* (2018.01); *H01L 21/0274* (2013.01); *G03F 7/162* (2013.01); *G03F 7/20* (2013.01); *G03F 7/30* (2013.01)

(58) Field of Classification Search
CPC ... G03F 7/11; G03F 7/162; G03F 7/20; G03F 7/30; G03F 7/094; G03F 7/004; G03F 7/26; C07D 251/24; C07D 405/14; C09D 7/63; H01L 21/0274; H01L 21/0332; H01L 21/027

USPC .............................................. 430/323, 270.1
See application file for complete search history.

(56) References Cited

U.S. PATENT DOCUMENTS

| | | |
|---|---|---|
| 5,976,512 A | 11/1999 | Huber |
| 2005/0129632 A1 | 6/2005 | Haase et al. |
| 2016/0016872 A1* | 1/2016 | Aqad ............... C07C 39/14 568/744 |

FOREIGN PATENT DOCUMENTS

| | | |
|---|---|---|
| JP | 10-251273 A | 9/1998 |
| JP | 2004177668 A | 6/2004 |
| JP | 2005532273 A | 10/2005 |
| JP | 2007114452 A | 5/2007 |
| JP | 2016018093 A | 2/2016 |
| KR | 1020100136227 A | 12/2010 |

OTHER PUBLICATIONS

International Search Report dated Dec. 11, 2018 in PCT/JP2018/041410 (with English translation).
Written Opinion dated Dec. 11, 2018 in PCT/JP2018/041410 (with English translation).
Office Action dated Jul. 26, 2022 in Japanese Patent Application No. 2019-554183 (with English translation), 6 pages.
Combined Office Action and Search Report dated Jul. 5, 2022 in Taiwanese Patent Application No. 107140078, received Aug. 3, 2022 (with English translation), 11 pages.

* cited by examiner

*Primary Examiner* — Caleen O Sullivan
(74) *Attorney, Agent, or Firm* — Element IP, PLC (57) ABSTRACT

A composition for resist underlayer film formation, includes a compound represented by formula (1) and a solvent. $Ar^1$ represents an aromatic heterocyclic group having a valency of m and having 5 to 20 ring atoms; m is an integer of 1 to 11; $Ar^2$ is a group bonding to a carbon atom of the aromatic heteroring in $Ar^1$ and represents an aromatic carbocyclic group having 6 to 20 ring atoms and having a valency of (n+1) or an aromatic heterocyclic group having 5 to 20 ring atoms and having a valency of (n+1); n is an integer of 0 to 12; and $R^1$ represents a monovalent organic group having 1 to 20 carbon atoms, a hydroxy group, a halogen atom, or a nitro group.

$$Ar^1(-Ar^2(-R^1)_n)_m \qquad (1)$$

20 Claims, 1 Drawing Sheet

COMPOSITION FOR RESIST UNDERLAYER FILM FORMATION, RESIST UNDERLAYER FILM AND FORMING METHOD THEREOF, PATTERNED SUBSTRATE-PRODUCING METHOD, AND COMPOUND

CROSS-REFERENCE TO RELATED APPLICATIONS

The present application is a continuation application of International Application No. PCT/JP2018/041410, filed Nov. 7, 2018, which claims priority to Japanese Patent Application No. 2017-221341, filed Nov. 16, 2017. The contents of these applications are incorporated herein by reference in their entirety.

BACKGROUND OF THE INVENTION

Field of Invention

The present invention relates to a composition for resist underlayer film formation, a resist underlayer film and a forming method thereof, a patterned substrate-producing method, and a compound.

Discussion of the Background

In manufacturing semiconductor devices, multilayer resist processes have been employed which include, for example: laminating a resist film to a substrate via a resist underlayer such as an organic underlayer film or a silicon-containing film; and exposing and developing the resist film to form a resist pattern. In these processes, the resist underlayer film is etched by using the resist pattern as a mask, and further, the substrate is etched by using the resultant resist underlayer film pattern as a mask, thereby enabling a desired pattern to be formed on the substrate. Accordingly, a patterned substrate can be obtained (see Japanese Unexamined Patent Application, Publication No. 2004-177668).

SUMMARY OF THE INVENTION

According to an aspect of the present invention, a composition for resist underlayer film formation, includes a compound represented by formula (1) and a solvent.

(1)

In the formula (1), $Ar^1$ represents an aromatic heterocyclic group having a valency of m and having 5 to 20 ring atoms; m is an integer of 1 to 11; $Ar^2$ is a group bonding to a carbon atom of the aromatic heteroring in $Ar^1$ and represents an aromatic carbocyclic group having 6 to 20 ring atoms and having a valency of (n+1) or an aromatic heterocyclic group having 5 to 20 ring atoms and having a valency of (n+1); n is an integer of 0 to 12, wherein in a case in which m is no less than 2, a plurality of $Ar^2$s are identical or different from each other, and a plurality of n's are identical or different from each other; and $R^1$ represents a monovalent organic group having 1 to 20 carbon atoms, a hydroxy group, a halogen atom, or a nitro group, wherein in a case in which $R^1$ is present in a plurality of number, a plurality of $R^1$s are identical or different from each other.

According to another aspect of the present invention, a resist underlayer film is formed from the composition.

According to further aspect of the present invention, a resist underlayer film-forming method includes applying the composition directly or indirectly on one face side of a substrate to form a coating film; and heating the coating film.

According to further aspect of the present invention, a patterned substrate-producing method includes applying a composition for resist underlayer film formation comprising a compound represented by formula (1) and a solvent, directly or indirectly on an upper face side of a substrate to form a coating film. The coating film is heated to form a resist underlayer film. A resist pattern is formed on an upper face side of the resist underlayer film. The substrate is etched using the resist pattern as a mask.

(1)

In the formula (1), $Ar^1$ represents an aromatic heterocyclic group having a valency of m and having 5 to 20 ring atoms; m is an integer of 1 to 11; $Ar^2$ is a group bonding to a carbon atom of the aromatic heteroring in $Ar^1$ and represents an aromatic carbocyclic group having 6 to 20 ring atoms and having a valency of (n+1) or an aromatic heterocyclic group having 5 to 20 ring atoms and having a valency of (n+1); n is an integer of 0 to 12, wherein in a case in which m is no less than 2, a plurality of $Ar^2$s are identical or different from each other, and a plurality of n's are identical or different from each other; and $R^1$ represents a monovalent organic group having 1 to 20 carbon atoms, a hydroxy group, a halogen atom, or a nitro group, wherein in a case in which $R^1$ is present in a plurality of number, a plurality of $R^1$s are identical or different from each other.

According further aspect of the present invention, a compound is represented by formula (1').

(1')

In the formula (1'), $Ar^1$ represents an aromatic heterocyclic group having a valency of m and having 5 to 20 ring atoms; m is an integer of 1 to 11; $Ar^2$ is a group bonding to a carbon atom of the aromatic heteroring in $Ar^1$ and represents an aromatic carbocyclic group having 6 to 20 ring atoms and having a valency of (n+1) or an aromatic heterocyclic group having 5 to 20 ring atoms and having a valency of (n+1); n is an integer of 0 to 12, wherein in a case in which m is no less than 2, a plurality of $Ar^2$s are identical or different from each other, and a plurality of n's are identical or different from each other; and $R^1$ represents a monovalent organic group having 1 to 20 carbon atoms, a hydroxy group, a halogen atom, or a nitro group, wherein in a case in which $R^1$ is present in a plurality of number, a plurality of $R^1$s are identical or different from each other, and wherein at least one $R^1$ represents an organic group, and at least one organic group represented by $R^1$ is a multiple bond-containing group.

DESCRIPTION OF EMBODIMENTS

The resist underlayer film for use in such a multilayer resist process is demanded to have resistance to organic solvents. Recently, there are increasing cases of pattern formation on a substrate having multiple types of trenches, particularly trenches with aspect ratios that are different from one another. In these cases, the composition for resist underlayer film formation is demanded to sufficiently fill these trenches and to be capable of forming a resist underlayer film having superior flatness.

Along with progress in microfabrication of a substrate pattern to be formed, the resist underlayer film has also been demanded to be superior in flexural resistance, accompanied by less bending of the underlayer film pattern when the substrate is etched using a formed underlayer film pattern as a mask.

According to one embodiment of the invention, a composition for resist underlayer film formation contains: a compound (hereinafter, may be also referred to as "(A) compound" or "compound (A)") represented by the following formula (1); and a solvent (hereinafter, may be also referred to as "(B) solvent" or "solvent (B)").

(1)

wherein, in the formula (1), $Ar^1$ represents an aromatic heterocyclic group having a valency of m and having 5 to 20 ring atoms; m is an integer of 1 to 11; $Ar^2$ is a group bonding to a carbon atom of the aromatic heteroring in $Ar^1$ and represents an aromatic carbocyclic group having 6 to 20 ring atoms and having a valency of (n+1) or an aromatic heterocyclic group having 5 to 20 ring atoms and having a valency of (n+1); n is an integer of 0 to 12, wherein in a case in which m is no less than 2, a plurality of $Ar^2$s are identical or different from each other, and a plurality of n's are identical or different from each other; and $R^1$ represents a monovalent organic group having 1 to 20 carbon atoms, a hydroxy group, a halogen atom, or a nitro group, wherein in a case in which $R^1$ is present in a plurality of number, a plurality of $R^1$s are identical or different from each other.

According to another embodiment of the invention, a resist underlayer film is formed from the composition for resist underlayer film formation of the one embodiment of the invention.

According to a further embodiment of the invention, a resist underlayer film-forming method includes:

a step of applying a composition for resist underlayer film formation containing the compound (A) and the solvent (B), directly or indirectly on one face side of a substrate; and a step of heating a coating film formed by the step of applying.

According to a still another embodiment of the invention, a patterned substrate-producing method includes:

a step of applying a composition for resist underlayer film formation containing the compound (A) and the solvent (B) directly or indirectly on an upper face side of a substrate;

a step of heating a coating film formed by the applying step;

a step of forming a resist pattern on an upper face side of a resist underlayer film formed by the heating step; and a step of etching the substrate using the resist pattern as a mask.

According to yet another embodiment of the invention, a compound is represented by the following formula (1'):

(1')

wherein, in the formula (1), $Ar^1$ represents an aromatic heterocyclic group having a valency of m and having 5 to 20 ring atoms; m is an integer of 1 to 11; $Ar^2$ is a group bonding to a carbon atom of the aromatic heteroring in $Ar^1$ and represents an aromatic carbocyclic group having 6 to 20 ring atoms and having a valency of (n+1) or an aromatic heterocyclic group having 5 to 20 ring atoms and having a valency of (n+1); n is an integer of 0 to 12, wherein in a case in which m is no less than 2, a plurality of $Ar^2$s are identical or different from each other, and a plurality of n's are identical or different from each other; and $R^1$ represents a monovalent organic group having 1 to 20 carbon atoms, a hydroxy group, a halogen atom, or a nitro group, wherein in a case in which $R^1$ is present in a plurality of number, a plurality of $R^1$s are identical or different from each other, and wherein at least one $R^1$ represents an organic group, and at least one of the organic group is a multiple bond-containing group.

The composition for resist underlayer film formation of the embodiment of the present invention enables formation of a resist underlayer film that is superior in flatness and flexural resistance of a pattern with resistance to organic solvents being maintained. The resist underlayer film of the embodiment of the present invention is superior in flatness and flexural resistance of a pattern, with resistance to organic solvents being maintained. The resist underlayer film-forming method of the embodiment of the present invention enables a resist underlayer film that is superior in flatness and flexural resistance of a pattern to be formed, with resistance to organic solvents being maintained. The patterned substrate-producing method of the embodiment of the present invention enables a favorable patterned substrate to be obtained by using such a superior resist underlayer film. The compound of the embodiment of the present invention can be suitably used as a component of the composition for resist underlayer film formation of the embodiment of the invention. Therefore, these can be suitably used for manufacture, etc., of semiconductor devices in which further progress of microfabrication is expected in the future. Hereinafter, the embodiments of the present invention will be described in detail.

Composition for Resist Underlayer Film Formation

The composition for resist underlayer film formation (hereinafter, may be (also) merely referred to as "composition") contains the compound (A) and the solvent (B). The composition may also contain optional component(s) within a range not leading to impairment of the effects of the present invention. The composition for forming a resist underlayer film can be suitably used for a multilayer resist process. Each component will be described in the following.

(A) Compound

The compound (A) is represented by the following formula (1).

(1)

In the above formula (1), $Ar^1$ represents an aromatic heterocyclic group having a valency of m and having 5 to 20 ring atoms; m is an integer of 1 to 11; $Ar^2$ is a group bonding to a carbon atom of the aromatic heteroring in $Ar^1$ and represents an aromatic carbocyclic group having 6 to 20 ring atoms and having a valency of (n+1) or an aromatic heterocyclic group having 5 to 20 ring atoms and having a valency of (n+1); n is an integer of 0 to 12, wherein in a case in which m is no less than 2, a plurality of $Ar^2$s are identical or different from each other, a plurality of n's are identical or different from each other; and $R^1$ represents a monovalent organic group having 1 to 20 carbon atoms, a hydroxy group, a halogen atom, or a nitro group, wherein in a case in which $R^1$ is present in a plurality of number, a plurality of $R^1$s are identical or different from each other.

Due to having the compound (A), the composition enables formation of a film that is superior in flatness and flexural resistance of a pattern with resistance to organic solvents being maintained. Although not necessarily clarified and without wishing to be bound by any theory, the reason for achieving the effects described above due to the composition having the aforementioned constitution may be supposed as in the following, for example. Specifically, it is considered that since the compound (A) has a structure in which one or a plurality of aromatic carbon rings or aromatic heterorings represented by $Ar^2$ are bonded to a central aromatic heteroring represented by $Ar^1$, a resist underlayer film to be formed is less likely to be thermally decomposed, and as a result, a resist underlayer film to be formed has improved flatness. In addition, it is believed that since the compound (A) has as central $Ar^1$, an aromatic heterocyclic group not having a hydrogen atom or having few hydrogen atoms, deterioration of strength, which results from a replacement reaction with fluorine atoms by a fluorine etching gas, of the resist underlayer film to be formed is less likely to occur, whereby flexural resistance of a resist underlayer film pattern may be improved.

Examples of the aromatic heterocyclic group having a valency of m and having 5 to 20 ring atoms represented by $Ar^1$ include groups obtained by removing m hydrogen atoms bonding to a carbon atom of an aromatic heteroring from, for example: a nitrogen atom-containing heterocyclic compound such as pyridine, quinoline, isoquinoline, indole, pyrazine, pyrimidine, pyridazine, or triazine; an oxygen atom-containing heterocyclic compound such as furan, pyran, benzofuran, or benzopyran; or a sulfur atom-containing heterocyclic compound such as thiophene or benzothiophene, and the like. Of these, a group derived from a nitrogen atom-containing heterocyclic compound is preferred, a group derived from triazine or pyrimidine is more preferred, and a group derived from triazine is still more preferred.

The lower limit of m is preferably 2, and more preferably 3. The upper limit of m is preferably 8, and more preferably 6.

$Ar^1$ represents preferably a triazinetriyl group, and more preferably a 1,3,5-triazinetriyl group. In this case, m is preferably 3.

$Ar^1$ may also have a substituent other than the group represented by —$Ar^1$—$(R^1)_n$.

Examples of the aromatic carbocyclic group having 6 to 20 ring atoms and having a valency of (n+1) which may be represented by $Ar^2$ include groups obtained by removing (n+1) hydrogen atoms bonding to a carbon atom of an aromatic carbon ring from, for example, an aromatic carbocyclic compound such as: benzene; naphthalene; anthracene; phenanthrene; tetracene; pyrene; triphenylene; or perylene, and the like. As the aromatic carbocyclic compound, benzene or naphthalene is preferred.

Examples of the aromatic heterocyclic group having 5 to 20 ring atoms and having a valency of (n+1) which may be represented by $Ar^2$ include groups obtained by removing (n+1) hydrogen atoms bonding to a carbon atom of an aromatic heteroring from, for example, the compound exemplified as the aromatic heterocyclic compound that gives $Ar^2$ described above, or the like. Of these, a group derived from pyridine or furan is preferred.

The lower limit of n is preferably 1, more preferably 2, and still more preferably 3. The upper limit of n is preferably 10, more preferably 8, and still more preferably 6.

It is preferred that at least one n in the above formula (1) is no less than 1, it is more preferred that at least two n's are each no less than 1, and it is still more preferred that at least three n's are each no less than 1. Due to having the group represented by $R^1$, the compound (A) may have further improved crosslinking reactivity, and as a result, flexural resistance of the pattern can be further improved.

$Ar^2$ represents preferably a group obtained by removing two to four hydrogen atoms from benzene, and more preferably a benzene-1,4-diyl group, a benzene-1,2,4-triyl group or a benzene-1,2,4,6-tetrayl group.

$Ar^2$ may also have a substituent other than the group represented by $R^1$.

The monovalent organic group having 1 to 20 carbon atoms which may be represented by $R^1$ is exemplified by: a monovalent hydrocarbon group having 1 to 20 carbon atoms; a group (α) that includes a divalent hetero atom-containing group between two adjacent carbon atoms of this hydrocarbon group, or between this hydrocarbon group and an atom constituting $Ar^2$; a group (β) obtained by substituting with a monovalent hetero atom-containing group, a part or all of hydrogen atoms included in the aforementioned hydrocarbon group or the group (α); a group (γ) that includes a divalent hetero atom-containing group between a monovalent hetero atom-containing group and an atom constituting $Ar^2$; and the like.

The monovalent hydrocarbon group having 1 to 20 carbon atoms is exemplified by a monovalent chain hydrocarbon group having 1 to 20 carbon atoms, a monovalent alicyclic hydrocarbon group having 3 to 20 carbon atoms, an aromatic hydrocarbon group having 6 to 20 carbon atoms monovalent, and the like.

Examples of the monovalent chain hydrocarbon group having 1 to 20 carbon atoms include groups obtained by removing one hydrogen atom from: an alkane such as methane, ethane, propane, or butane; an alkene such as ethene, propene, or butene; an alkyne such as ethyne, propyne, or butyne, and the like.

Examples of the monovalent alicyclic hydrocarbon group having 3 to 20 carbon atoms include groups obtained by removing one hydrogen atom from: alicyclic saturated hydrocarbons, e.g., a cycloalkane such as cyclopentane or cyclohexane, or a bridged cyclic saturated hydrocarbons such as norbornane, adamantane or tricyclodecane; or alicyclic unsaturated hydrocarbons, e.g., a cycloalkene such as cyclopentene or cyclohexene, or a crosslinked cyclic unsaturated hydrocarbon such as norbornene or tricyclodecene, and the like.

Examples of the monovalent aromatic hydrocarbon group having 6 to 20 carbon atoms include groups obtained by removing a hydrogen atom on 2 to 4 aromatic rings, or a hydrogen atom on an aromatic ring and an alkyl group of an arene such as benzene, toluene, ethylbenzene, xylene, naphthalene, methylnaphthalene, anthracene, methylanthracene, or pyrene and the like.

Examples of the hetero atom constituting the divalent or monovalent hetero atom-containing group include an oxygen atom, a nitrogen atom, a sulfur atom, a phosphorus atom, a silicon atom, a halogen atom, and the like. Examples of the halogen atom include a fluorine atom, a chlorine atom, a bromine atom, and an iodine atom.

The divalent hetero atom-containing group is exemplified by —O—, —CO—, —S—, —CS—, —NR'—, a group obtained by combining two or more of these, or the like, wherein R' represents a hydrogen atom or a monovalent hydrocarbon group.

Examples of the monovalent hetero atom-containing group include halogen atoms such as a fluorine atom, a chlorine atom, a bromine atom and an iodine atom, a hydroxy group, a carboxy group, a cyano group, an amino group, a sulfanyl group, an epoxy group, and the like.

It is preferred that at least one $R^1$ in the above formula (1) represents an organic group. The lower limit of the number of the organic group as $R^1$ in the compound (A) is preferably 2, more preferably 5, and still more preferably 8. The upper limit of the number of the organic group is preferably 20, and more preferably 15.

It is preferred that at least one organic group which may be represented by $R^1$ is a multiple bond-containing group. When the multiple bond-containing group is included as $R^1$, a proportion of hydrogen atoms contained in the compound (A) can be further decreased, and as a result, flexural resistance of the pattern can be further improved. The term "multiple bond-containing group" as referred to herein means a group that includes a double bond or a triple bond between two atoms. The double bond may include a conjugated double bond in an aromatic carbon ring or an aromatic heteroring.

The multiple bond-containing group is exemplified by a carbon-carbon double bond-containing group, a carbon-carbon triple bond-containing group, a carbon-nitrogen double bond-containing group, a carbon-nitrogen triple bond-containing group, a carbon-oxygen double bond-containing group, and the like.

Examples of the carbon-carbon double bond-containing group include: ethylenic double bond-containing groups such as a vinyl group, a vinyloxy group, an allyl group, an allyloxy group, a (meth)acryloyl group, and a (meth)acryloyloxy group; aromatic hydrocarbon groups such as a phenyl group and a naphthyl group; groups obtained from these groups by substituting a part or all of hydrogen atoms with a hydroxy group, a halogen atom, a monovalent organic group or the like (hereinafter, these may be also referred to as "substituent (a)"); and the like. Of these, the allyloxy group is preferred.

Examples of the carbon-carbon triple bond-containing group include: a propargyl group, a propargyloxy group; groups obtained from these groups by substituting a part or all of hydrogen atoms with the substituent (a); an ethynyl group; an ethynyloxy group; and the like. Of these, a propargyloxy group is preferred.

Examples of the carbon-nitrogen double bond-containing group include: imino-containing groups such as a methylimino group; nitrogen-containing heterocyclic groups such as a pyridyl group, a pyrazinyl group, a pyrimidinyl group, and a triazinyl group; groups obtained from these groups by substituting a part or all of hydrogen atoms with the substituent (a); and the like. Of these, a triazinyl group and a diphenyl triazinyl group are preferred.

Examples of the carbon-nitrogen triple bond-containing group include: cyanoalkyl groups such as a cyanomethyl group; cyanoalkyloxy groups such as a cyanomethyloxy group; cyanoaryl groups such as a cyanophenyl group; cyanoaryloxy groups such as a cyanophenyloxy group; groups obtained from these groups by substituting a part or all of hydrogen atoms with the substituent (a); a cyano group; a cyanate group; and the like. Of these, the cyanoalkyloxy group, the cyanoaryloxy group, a cyano group and a cyanate group are preferred, and a cyanomethyloxy group, a cyanophenyloxy group and a cyanate group are more preferred.

Examples of the carbon-oxygen double bond-containing group include: acyl groups such as a formyl group and an acetyl group; acyloxy groups such as a formyloxy group and an acetyloxy group; alkoxycarbonyl groups such as a methoxycarbonyl group: aryloxycarbonyl groups such as a phenoxy carbonyl group; groups obtained from these groups by substituting a part or all of hydrogen atoms with the substituent (a); and the like. Of these, the acyloxy group is preferred, and an acetyloxy group is more preferred.

It is also preferred that the organic group which may be represented by $R^1$ is a crosslinkable substituent. When the compound (A) has the crosslinkable substituent, crosslinking reactivity may be further improved, and as a result, flexural resistance of the pattern is further improved. The "crosslinkable substituent" as referred to herein means a substituent that is capable of forming a crosslinking bond that crosslinks in the compound (A), between the compounds (A) or between the compound (A) and other compound by a reaction between the crosslinkable substituents or a reaction of the crosslinkable substituent with other substituent.

The crosslinkable substituent is exemplified by the ethylenic double bond-containing group, the carbon-carbon triple bond-containing group, the imino-containing group, the carbon-nitrogen triple bond-containing group, the acyl group, and the acyloxy group, as well as, for example, an epoxy group, a hydroxy chain hydrocarbon group, and the like.

Examples of the epoxy group include: oxirane ring-containing groups such as an oxiranyl group, an oxiranylmethyl group, and an oxiranylmethyloxy group; oxetane ring-containing groups such as an oxetanyl group, an oxetanylmethyl group, and an oxetanylmethyloxy group; groups obtained from these groups by substituting a part or all of hydrogen atoms with the substituent (a); and the like.

Examples of the hydroxy chain hydrocarbon group include hydroxyalkyl groups such as a hydroxymethyl group, a 1-hydroxyethyl group, a 1-hydroxypropyl group, and a 2-hydroxy-2-propyl group, and the like.

Also, a group represented by the following formula (2) is preferred as the organic group which may be represented by $R^1$.

$$*-X-R^{1'} \quad (2)$$

In the above formula (2), X represents a single bond or a divalent hetero atom-containing group; $R^{1'}$ represents a monovalent hydrocarbon group having 1 to 20 carbon atoms, a monovalent hetero atom-containing group, or a group obtained by substituting with a monovalent hetero atom-containing group, a part or all of hydrogen atoms included in the hydrocarbon group; and * denotes a bonding site to $Ar^2$.

Examples of the divalent hetero atom-containing group which may be represented by X include groups similar to the divalent hetero atom-containing group for the organic group which may be represented by $R^1$ described above, and the like. Examples of the group obtained by substituting with a monovalent hetero atom-containing group, a part or all of hydrogen atoms included in the hydrocarbon group, the monovalent hetero atom-containing group, or the hydrocarbon group which may be represented by $R^{1'}$ include groups similar to the group obtained by substituting with a monovalent hetero atom-containing group, a part or all of hydrogen atoms included in the hydrocarbon group, the monovalent hetero atom-containing group, or the hydrocarbon group which may be represented by $R^1$ described above, and the like.

Examples of the compound (A) include compounds represented by the following formulae (i-1) and (i-2), and the like.

(i-1)

(i-2)

In the above formulae (i-1) and (i-2), $Ar^{1A}$ and $Ar^{1B}$ each independently represent a trivalent aromatic heterocyclic group having 5 to 20 ring atoms; $Ar^{2A}$ to $Ar^{2E}$ are each independently a group bonding to a carbon atom of the aromatic heterering in $Ar^{1A}$ or $Ar^{1B}$, and each represent an aromatic carbocyclic group having 6 to 20 ring atoms or an aromatic heterocyclic group having 5 to 20 ring atoms; n1 to n5 are each independently an integer of 1 to 11; $Ar^{2'}$ is a group bonding to the aromatic heterering in $Ar^{1B}$, and represents a monovalent aromatic carbocyclic group having 6 to 20 ring atoms or a monovalent aromatic heterocyclic group having 5 to 20 ring atoms; and $R^{1A}$ to $R^{1E}$ each independently represent a monovalent organic group having 1 to 20 carbon atoms, a hydroxy group, a halogen atom, or a nitro group, wherein in a case in which n1 is no less than 2, a plurality of $R^{1A}$s are identical or different from each other, in a case in which n2 is no less than 2, a plurality of $R^{1B}$s are identical or different from each other, in a case in which n3 is no less than 2, a plurality of $R^{1C}$s are identical or different from each other, in a case in which n4 is no less than 2, a plurality of $R^{1D}$s are identical or different from each other, and in a case in which n5 is no less than 2, a plurality of $R^{1E}$s are identical or different from each other.

In the above formula (i-2), Ar represents preferably an aromatic carbocyclic group, and more preferably a phenyl group or a pyrenyl group.

As the compound (A), a compound represented by the following formula (1') (hereinafter, may be also referred to as "compound (I)") is preferred.

(1')

In the above formula (1'), $Ar^1$ represents an aromatic heterocyclic group having a valency of m and having 5 to 20 ring atoms; m is an integer of 1 to 11; $Ar^2$ is a group bonding to a carbon atom of the aromatic heterering in $Ar^1$ and represents an aromatic carbocyclic group having 6 to 20 ring atoms and having a valency of (n+1) or an aromatic heterocyclic group having 5 to 20 ring atoms and having a valency of (n+1); n is an integer of 0 to 12, wherein in a case in which m is no less than 2, a plurality of $Ar^2$s are identical or different from each other, and a plurality of n's are identical or different from each other; and $R^1$ represents a monovalent organic group having 1 to 20 carbon atoms, a hydroxy group, a halogen atom, or a nitro group, wherein in a case in which $R^1$ is present in a plurality of number, a plurality of $R^1$s are identical or different from each other, provided that at least one $R^1$ represents an organic group, and at least one of the organic group is a multiple bond-containing group.

$Ar^1$ may also have a substituent other than the group represented by —$Ar^2$—$(R^1)_n$. $Ar^2$ may also have a substituent other than the group represented by $R^1$.

The compound (I) is an example of the compound (A), wherein at least one $R^1$ represents an organic group, and at least one of the organic group is a multiple bond-containing group. Due to having such a structure, the compound (I) has further improved crosslinking reactivity, and as a result, flexural resistance of the pattern can be further improved.

The lower limit of a molecular weight of the compound (A) is preferably 300, and more preferably 400. The upper limit of the molecular weight is preferably 2,000, and more preferably 1,000. When the molecular weight of the compound (A) falls within the above range, flatness of the resist underlayer film can be further improved. The compound (A) may be used alone of one type, or two or more types thereof may be used in combination. In the case in which two or more types of the compound (A) are used, the molecular weight of the compound (A) as referred to is a number average molecular weight.

Synthesis Method of Compound (A)

The compound (A) can be synthesized by, for example: allowing for a dehydrohalogenation condensation reaction of an aromatic heterering-containing halide that gives $Ar^1$ such as cyanuric chloride, 1-(dichloro-1,3,5-triazinyl)pyrene, or 2,4-dichloro-6-phenyl-1,3,5-triazine with a phenol compound that gives $Ar^2$ such as phloroglucinol or resorcinol in the presence of a Lewis acid such as aluminum chloride, in a solvent such as diethyl ether, 1,2-dichloroethane, or cyclopentyl methyl ether to synthesize the compound (a) in which the aromatic carbocyclic group or the aromatic heterocyclic group including a phenolic hydroxyl group $Ar^2$ bonds to the aromatic heterocyclic group of $Ar^1$; and converting a hydrogen atom of the phenolic hydroxyl group of the resulting compound (a) into the group $R^1$ using propargyl bromide, bromoacetonitrile, cyanogen bromide, allyl bromide, 4-fluorobenzonitrile or the like in the presence of a base such as potassium carbonate or triethylamine in a solvent such as N,N-dimethylacetamide or tetrahydrofuran. 2,4,6-Tri(4-hydroxyphenyl)-1,3,5-triazine as the compound (a) can be synthesized also by trimerizing 4-cyanophenol in the presence of an acid such as trifluoromethanesulfonic acid in a solvent such as dichloromethane. Alternatively, the conversion of the hydrogen atom of the phenolic hydroxyl group into an acetyl group may be carried out using acetic anhydride in a solvent such as pyridine.

The upper limit of a proportion of hydrogen atoms contained in the compound (A) is preferably 6.5% by mass, more preferably 6.0% by mass, still more preferably 5.0% by mass, and particularly preferably 4.0% by mass. The lower limit of the proportion of hydrogen atoms contained is, for example, 0.1% by mass. When the proportion of hydrogen atoms contained in the compound (A) falls within the above range, flexural resistance of the pattern can be further improved.

The lower limit of a proportion of the compound (A) contained with respect to total components other than the solvent (B) in of the composition is preferably 50% by mass, more preferably 70% by mass, and still more preferably 85% by mass. The upper limit of the proportion is, for example, 100% by mass.

(B) Solvent

The solvent (B) is not particularly limited as long as it can dissolve or disperse the compound (A), and the optional component(s) which may be contained as needed.

The solvent (B) is exemplified by an alcohol solvent, a ketone solvent, an ether solvent, an ester solvent, a nitrogen-containing solvent, and the like. The solvent (B) may be used alone of one type, or two or more types thereof may be used in combination.

Examples of the alcohol solvent include: monohydric alcohol solvents such as methanol, ethanol and n-propanol; polyhydric alcohol solvents such as ethylene glycol and 1,2-propylene glycol; and the like.

Examples of the ketone solvent include: chain ketone solvents such as methyl ethyl ketone and methyl isobutyl ketone; cyclic ketone solvents such as cyclohexanone; and the like.

Examples of the ether solvent include: polyhydric alcohol ether solvents, e.g., chain ether solvents such as n-butyl ether, and cyclic ether solvents such as tetrahydrofuran; polyhydric alcohol partial ether solvents such as diethylene glycol monomethyl ether; and the like.

Examples of the ester solvent include: carbonate solvents such as diethyl carbonate; mono ester acetate solvents such as methyl acetate and ethyl acetate; lactone solvents such as γ-butyrolactone; polyhydric alcohol partial ether carboxylate solvents such as diethylene glycol monomethyl ether acetate and propylene glycol monomethyl ether acetate; ester lactate solvents such as methyl lactate and ethyl lactate; and the like.

Examples of the nitrogen-containing solvent include: chain nitrogen-containing solvents such as N,N-dimethylacetamide; cyclic nitrogen-containing solvents such as N-methylpyrrolidone; and the like.

The solvent (B) preferably contains the ether solvent and the ester solvent, and in light of superior film formability, it is more preferred that the solvent (B) contains the ether solvent and the ester solvent each having a glycol structure.

Examples of the ether solvent and the ester solvent each having a glycol structure include propylene glycol monomethyl ether, propylene glycol monoethyl ether, propylene glycol monopropyl ether, propylene glycol monomethyl ether acetate, propylene glycol monoethyl ether acetate, propylene glycol monopropyl ether acetate, and the like. Of these, propylene glycol monomethyl ether acetate is particularly preferred.

In the case in which the solvent (B) contains the ether solvent and the ester solvent each having a glycol structure, the lower limit of a proportion of the ether solvent and the ester solvent, each having a glycol structure, contained in the solvent (B) is preferably 20% by mass, more preferably 60% by mass, still more preferably 90% by mass, and particularly preferably 100% by mass.

The lower limit of a proportion of the solvent (B) in the composition is preferably 50% by mass, more preferably 70% by mass, and still more preferably 85% by mass. The upper limit of the proportion is preferably 99% by mass, and more preferably 95% by mass.

Optional Components The composition may contain as optional component(s), an acid generating agent, a crosslinking agent, a surfactant, an adhesion aid, and/or the like. These optional components may be used alone of one type, or two or more types thereof may be used in combination.

Acid Generating Agent

The acid generating agent generates an acid by an action of heat and/or light to promote the crosslinking of molecules of the compound (A). When the composition contains the acid generating agent, a crosslinking reaction of molecules of the compound (A) is promoted and consequently the hardness of the resist underlayer film to be formed can be further increased. The acid generating agent may be used alone of one type, or two or more types thereof may be used in combination.

The acid generating agent is exemplified by an onium salt compound, an N-sulfonyloxyimide compound, and the like.

Crosslinking Agent

The crosslinking agent forms crosslinking bonds between components such as the compound (A) in the composition, or forms cross-linked structures by its own molecules, through an action of heat and/or an acid. When the composition contains the crosslinking agent, an increase in hardness of the resist underlayer film to be formed is enabled.

The crosslinking agent may be used alone of one type, or two or more types thereof may be used in combination.

The crosslinking agent is exemplified by a polyfunctional (meth)acrylate compound, an epoxy compound, a hydroxymethyl group-substituted phenol compound, an alkoxyalkyl group-containing phenol compound, a compound having an alkoxyalkylated amino group, and the like.

Preparation Procedure of Composition

The composition may be prepared, for example, by mixing the compound (A), the solvent (B), and as needed, the optional component(s) in a certain ratio, preferably followed by filtering a thus resulting mixture through a membrane filter, etc. having a pore size of no greater than 0.1 μm.

Resist Underlayer Film

The resist underlayer film of the embodiment of the invention is formed from the composition of the embodiment of the present invention. Since the resist underlayer film is formed from the composition described above, the resist underlayer film is superior in flatness and flexural resistance of the pattern, with resistance to organic solvents being maintained.

Resist Underlayer Film-Forming Method

The resist underlayer film-forming method includes: a step of applying the composition of the embodiment of the invention directly or indirectly on one face side of a substrate (hereinafter, may be also referred to as "applying step"); and a step of heating a coating film formed by the applying step (hereinafter, may be also referred to as "heating step").

Since the composition described above is used in the resist underlayer film-forming method, a resist underlayer film that is superior in flatness and flexural resistance of a pattern can formed, with resistance to organic solvents being maintained. Hereinafter, each step will be described.

Applying Step

In this step, the composition of the embodiment of the invention is applied directly or indirectly on one face side of a substrate to form a coating film.

Examples of the substrate include a silicon wafer, a wafer coated with aluminum, and the like. The applying procedure of the composition is not particularly limited, and for example, an appropriate procedure such as spin coating, cast coating and roll coating may be employed to form the coating film.

Heating Step

In this step, the coating film formed by the applying step is heated to form a resist underlayer film.

Heating of the coating film is typically carried out in an ambient air, but may be carried out in a nitrogen atmosphere. A heating temperature is, for example, no less than 200° C. and no greater than 600° C. A heating time period is, for example, no less than 15 sec and no greater than 1,200 sec.

The coating film may be preheated at a temperature of no less than 60° C. and no greater than 150° C. before being heated at a temperature of no less than 200° C. and no greater than 600° C. The lower limit of the heating time period in the preheating is preferably 10 sec, and more preferably 30 sec. The upper limit of the heating time period is preferably 300 sec, and more preferably 180 sec.

It is to be noted that in the resist underlayer film-forming method of the embodiment of the invention, the resist underlayer film is formed through the heating of the coating film; however, in a case in which the composition contains the acid generating agent and the acid generating agent is a radiation-sensitive acid generating agent, it is also possible to form the resist underlayer film by hardening the film through a combination of an exposure and heating. The radioactive ray used for the exposure may be appropriately selected from: electromagnetic waves such as visible rays, ultraviolet rays, far ultraviolet rays, X-rays and γ-rays; and particle rays such as electron beams, molecular beams and ion beams in accordance with the type of the acid generating agent.

The lower limit of the average thickness of the resist underlayer film to be formed is preferably 30 nm, more preferably 50 nm, and still more preferably 100 nm. The upper limit of the average thickness is preferably 3,000 nm, more preferably 2,000 nm, and still more preferably 500 nm.

Patterned Substrate-Producing Method

The patterned substrate-producing method of the embodiment of the present invention includes: a step of applying the composition of the embodiment of the invention directly or indirectly on an upper face side of a substrate (applying step); a step of heating a coating film formed by the applying step (heating step); a step of forming a resist pattern on an upper face side of a resist underlayer film formed by the heating step (hereinafter, may be also referred to as "resist pattern-forming step"); and a step of etching the substrate using the resist pattern as a mask (hereinafter, may be also referred to as "etching step").

According to the patterned substrate-producing method, use of the aforementioned resist underlayer film being superior in flatness and flexural resistance of a pattern superior, with resistance to organic solvents being maintained, enables a favorable patterned substrate having a favorable pattern configuration to be obtained.

The patterned substrate-producing method may also include as needed, a step of forming a silicon-containing film on an upper face side of the resist underlayer film formed by the heating step (hereinafter, may be also referred to as "silicon-containing film-forming step"). Hereinafter, each step will be described.

Applying Step

In this step, the composition of the embodiment of the invention is applied directly or indirectly on an upper face side of a substrate to form a coating film. This step is similar to the applying step in the resist underlayer film-forming method described above.

Heating Step

In this step, the coating film formed by the applying step is heated to form a resist underlayer film. This step is similar to the heating step in the resist underlayer film-forming method described above.

Silicon-Containing Film-Forming Step

In this step, a silicon-containing film is formed on an upper face side of the resist underlayer film formed by the heating step.

The silicon-containing film may be formed by applying of a silicon-containing composition for film formation, a chemical vapor deposition (CVD) process, atom layer deposition (ALD), or the like. An exemplary procedure for forming the silicon-containing film by applying the silicon-containing composition for film formation includes, for example: applying a composition for silicon-containing film formation on an upper face side of the resist underlayer film to form a coating film; and hardening the coating film typically by subjecting the coating film to an exposure and/or heating. As a commercially available product of the composition for silicon-containing film formation, for example, "NFC SOG01", "NFC SOG04", or "NFC SOG080" (all available from JSR Corporation), or the like may be used. A silicon oxide film, a silicon nitride film, a silicon oxynitride film, or an amorphous silicon film can be formed by the chemical vapor deposition (CVD) process or atom layer deposition (ALD).

Examples of the radioactive ray for use in the exposure include: electromagnetic waves such as visible rays, ultraviolet rays, far ultraviolet rays, X-rays and γ-rays; particle rays such as electron beams, molecular beams and ion beams; and the like.

The lower limit of a temperature for heating the coating film is preferably 90° C., more preferably 150° C., and still more preferably 200° C. The upper limit of the temperature is preferably 550° C., more preferably 450° C., and still more preferably 300° C. The lower limit of an average thickness of the silicon-containing film to be formed is preferably 1 nm, more preferably 10 nm, and still more preferably 20 nm. The upper limit of the average thickness is preferably 20,000 nm, more preferably 1,000 nm, and still more preferably 100 nm.

Resist Pattern-Forming Step

In this step, a resist pattern is formed on an upper face side of the resist underlayer film described above. This step may be carried out by, for example, using a resist composition, or the like. It is to be noted that in the case in which the patterned substrate-producing method includes the silicon-containing film-forming step, the resist pattern is formed on an upper face side of the silicon-containing film in this resist pattern-forming step.

When the resist composition is used, specifically, the resist film is formed by applying the resist composition such that a resultant resist film has a predetermined thickness, and thereafter subjecting the resist composition to prebaking to evaporate away the solvent in the coating film.

Examples of the resist composition include a chemically amplified positive or negative resist composition that contains a radiation-sensitive acid generating agent; a positive resist composition containing an alkali-soluble resin and a quinone diazide-based photosensitizing agent; a negative resist composition containing an alkali-soluble resin and a crosslinking agent; and the like.

The lower limit of a concentration of the resist composition is preferably 0.3% by mass, and more preferably 1% by mass. The upper limit of the concentration of the resist composition is preferably 50% by mass, and more preferably 30% by mass. Moreover, the resist composition is generally used for forming a resist film, for example, after being filtered through a filter with a pore size of no greater than 0.2 μm. It is to be noted that a commercially available resist composition may be used as is in this step.

The applying procedure of the resist composition is not particularly limited, and examples thereof include a spin-coating procedure, and the like. The temperature of the prebaking may be appropriately adjusted in accordance with the type of the resist composition employed and the like; however, the lower limit of the temperature is preferably 30° C., and more preferably 50° C. The upper limit of the aforementioned temperature is preferably 200° C., and more preferably 150° C. The lower limit of a time period for the prebaking is preferably 10 sec, and more preferably 30 sec. The upper limit of the time period for the prebaking is preferably 600 sec, and more preferably 300 sec.

Next, the resist film formed is exposed by selective irradiation with a radioactive ray. The radioactive ray used in the exposure may be appropriately selected from: electromagnetic waves such as visible rays, ultraviolet rays, far ultraviolet rays, X-rays and γ-rays; and particle rays such as electron beams, molecular beams and ion beams in accordance with the type of the radiation-sensitive acid generating agent to be used in the resist composition. Among these, far ultraviolet rays are preferred, a KrF excimer laser beam (248 nm), an ArF excimer laser beam (193 nm), an $F_2$ excimer laser beam (wavelength: 157 nm), a $Kr_2$ excimer laser beam (wavelength: 147 nm), an ArKr excimer laser beam (wavelength: 134 nm) and an extreme ultraviolet ray (EUV; wavelength: 13.5 nm, etc.) are more preferred, and a KrF excimer laser beam, an ArF excimer laser beam and EUV are still more preferred.

Post-baking may be carried out after the exposure for the purpose of improving resolution, pattern profile, developability, and the like. The temperature of the post-baking may be appropriately adjusted in accordance with the type of the resist composition to be employed and the like; however, the lower limit of the temperature is preferably 50° C., and more preferably 70° C. The upper limit of the aforementioned temperature is preferably 200° C., and more preferably 150° C. The lower limit of a time period for the post-baking is preferably 10 sec, and more preferably 30 sec. The upper limit of the time period for the post-baking is preferably 600 sec, and more preferably 300 sec.

Next, the resist film exposed is developed with a developer solution to form a resist pattern. The development may be either a development with an alkali or a development with an organic solvent. In the case of the development with an alkali, examples of the developer solution include a basic aqueous solution that contains sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethylethanolamine, triethanolamine, tetramethylammonium hydroxide (TMAH), tetraethylammonium hydroxide, pyrrole, piperidine, choline, 1,8-diazabicyclo[5.4.0]-7-undecene, 1,5-diazabicyclo[4.3.0]-5-nonene, or the like. An appropriate amount of a water-soluble organic solvent, e.g., an alcohol such as methanol or ethanol, a surfactant, or the like may be added to the basic aqueous solution. Alternatively, in the case of the development with an organic solvent, examples of the developer solution include a variety of organic solvents exemplified as the solvent (B) in relation to the composition described above, and the like.

A predetermined resist pattern is formed by the development with the developer solution, followed by washing and drying.

In carrying out the resist pattern-forming step, aside from using the resist composition described above, another process may be employed; for example, a nanoimprinting procedure may be adopted, or a directed self-assembling composition may be also used.

Etching Step

In this step, the substrate is etched with the aforementioned resist pattern as a mask to form a pattern on the substrate. The etching may be conducted once or multiple times. In other words, the etching may be conducted sequentially with patterns obtained by the etching as masks. However, in light of obtaining a pattern with a more favorable configuration, the etching is preferably conducted multiple times. In the case in which the etching is conducted multiple times, the silicon-containing film, the film, and the substrate are subjected to the etching sequentially in this order. The etching step may be exemplified by dry etching, wet etching, and the like. Of these, in light of achieving a pattern with a more favorable configuration, dry etching is preferred. For example, gas plasma such as oxygen plasma or the like may be used in the dry etching. After the dry etching, the substrate having a predetermined pattern can be obtained.

EXAMPLES

Hereinafter, the embodiment of the present invention will be explained in more detail by way of Examples, but the present invention is not in any way limited to these Examples. Measuring methods for various types of physical properties are shown below.

Average Thickness of Resist Underlayer Film

The average thickness of the resist underlayer film was measured by using a spectroscopic ellipsometer ("M2000D" available from J. A. WOOLLAM Co.).

Synthesis of Compound (A)

Compounds represented by the following formulae (A-1) to (A-10) (hereinafter, may be also referred to as "compound (A-1) to (A-10)") as the compound (A) were synthesized in accordance with the following procedure.

(A-1)

(A-2)

17
-continued

(A-3)

(A-4)

(A-5)

18
-continued

(A-6)

(A-7)

(A-8)

-continued (A-9)

(A-10)

Example 1-1

Into a reaction container, 23.2 g of cyanuric chloride, 50.0 g of phloroglucinol, 586 g of diethyl ether, and 146 g of 1,2-dichloroethane were added and dissolution was allowed in a nitrogen atmosphere. After cooling the mixture to 0° C. and then adding thereto 52.9 g of aluminum chloride, the reaction was allowed at 40° C. for 12 hrs. The reaction solution was concentrated to eliminate diethyl ether, and charged into a large amount of a 10% by mass hydrochloric acid to permit reprecipitation. After a thus resulting precipitate was dissolved in 300 g of dimethylformamide and 300 g of methanol, the mixture was charged into a large amount of a 10% by mass hydrochloric acid to permit reprecipitation. After a thus resulting precipitate was dispersed in 500 g of ethanol, neutralization with triethylamine, followed by recovery of the precipitate through filtration and drying gave 50.2 g of a compound represented by the following formula (a-1) (hereinafter, may be also referred to as "compound (a-1)").

(a-1)

Into a reaction container, 20.0 g of the compound (a-1), 120 g of N,N-dimethylacetamide, and 60.4 g of potassium carbonate were added in a nitrogen atmosphere. Next, the mixture was warmed to 50° C., and thereto was added 52.0 g of propargyl bromide and a reaction was allowed for 12 hrs. To the reaction solution, 40 g of methyl isobutyl ketone, 40 g of tetrahydrofuran, and 240 g of water were added, and after liquid separation extraction was conducted, the organic layer was charged into a large amount of hexane to permit reprecipitation. Filtration of the mixture followed by recovery and drying of the precipitate gave 28.2 g of the compound (A-1).

Example 1-2

Into a reaction container, 26.6 g of cyanuric chloride, 50.0 g of resorcinol, and 766 g of 1,2-dichloroethane were added and dissolution was allowed in a nitrogen atmosphere. After cooling the mixture to 0° C. and then adding thereto 60.6 g of aluminum chloride, the reaction was allowed for 6 hrs by warming to 60° C. The reaction solution was charged into a large amount of a 10% by mass hydrochloric acid to permit reprecipitation. After a thus resulting precipitate was dissolved in 300 g of dimethylformamide and 300 g of methanol, the mixture was charged into a large amount of a 10% by mass hydrochloric acid to permit reprecipitation. After a thus resulting precipitate was dispersed in 500 g of ethanol, neutralization with triethylamine, followed by recovery of the precipitate through filtration and drying gave 42.8 g of a compound represented by the following formula (a-2) (hereinafter, may be also referred to as "compound (a-2)").

(a-2)

Into a reaction container, 20.0 g of the compound (a-2), 120 g of N,N-dimethylacetamide, and 45.0 g of potassium carbonate were added in a nitrogen atmosphere. Next, the mixture was warmed to 50° C. and thereto was added 38.7 g of propargyl bromide, and a reaction was allowed for 12 hrs. To the reaction solution, 40 g of methyl isobutyl ketone, 40 g of tetrahydrofuran, and 240 g of water were added and after liquid separation extraction was conducted, the organic phase was charged into a large amount of hexane to permit reprecipitation. Filtration of the mixture followed by recovery and drying of the precipitate gave 22.3 g of the compound (A-2).

Example 1-3

Into a reaction container, 26.5 g of 1-(dichloro-1,3,5-triazinyl)pyrene, 20.0 g of phloroglucinol, and 465 g of cyclopentyl methyl ether were added and dissolution was allowed in a nitrogen atmosphere. After cooling the mixture to 0° C. and then adding thereto 60.6 g of aluminum chloride, the reaction was allowed for 8 hrs by warming to 60° C. The reaction solution was charged into a large amount of a 10% by mass hydrochloric acid to permit reprecipitation. A thus resulting precipitate was washed in methanol/water (400 g/400 g), and filtration of the mixture followed by recovery and drying of the precipitate gave 32.4 g of a compound represented by the following formula (a-3) (hereinafter, may be also referred to as "compound (a-3)").

(a-3)

Into a reaction container, 10.0 g of the compound (a-3), 60 g of N,N-dimethylacetamide, and 17.2 g of potassium carbonate were added in a nitrogen atmosphere. The mixture was warmed to 60° C. and thereto was added 14.8 g of propargyl bromide, and a reaction was allowed for 12 hrs. To the reaction solution, 40 g of methyl isobutyl ketone, 40 g of tetrahydrofuran, and 240 g of water were added, and after liquid separation extraction was conducted, the organic phase was charged into a large amount of hexane to permit reprecipitation. Filtration of the mixture followed by recovery and drying of the precipitate gave 9.9 g of the compound (A-3).

Example 1-4

Into a reaction container, 48.9 g of 2,4-dichloro-6-phenyl-1,3,5-triazine, 50.0 g of resorcinol, and 465 g of cyclopentyl methyl ether were added and dissolution was allowed in a nitrogen atmosphere. After cooling the mixture to 0° C. and then adding thereto 60.6 g of aluminum chloride, the reaction was allowed for 8 hrs by warming to 60° C. The reaction solution was charged into a large amount of a 10% by mass hydrochloric acid to permit reprecipitation. A thus resulting precipitate was washed in methanol/water (400 g/400 g), and filtration of the mixture followed by recovery and drying of the precipitate gave 62.9 g of a compound represented by the following formula (a-4) (hereinafter, may be also referred to as "compound (a-4)").

(a-4)

Into a reaction container, 20.0 g of the compound (a-4), 120 g of N,N-dimethylacetamide, and 23.0 g of potassium carbonate were added in a nitrogen atmosphere. The mixture was warmed to 60° C. and thereto was added 19.8 g of propargyl bromide, and a reaction was allowed for 12 hrs. To the reaction solution, 40 g of methyl isobutyl ketone, 40 g of tetrahydrofuran, and 240 g of water were added, and after liquid separation extraction was conducted, the organic phase was charged into a large amount of hexane to permit reprecipitation. Filtration of the mixture followed by recovery and drying of the precipitate gave 19.3 g of the compound (A-4).

Example 1-5

In a similar manner to Example 1-1 except that 52.0 g of propargyl bromide in Example 1-1 was changed to 52.4 g of bromoacetonitrile, 25.1 g of the compound (A-5) was obtained.

Example 1-6

Into a reaction container, 20.0 g of the compound (a-1), 240 g of tetrahydrofuran, and 44.2 g of triethylamine were added in a nitrogen atmosphere. Thereafter, the mixture was cooled to 0° C. and thereto was added 46.3 g of cyanogen bromide dropwise, and a reaction was allowed for 6 hrs. To the reaction solution, 40 g of methyl isobutyl ketone and 240 g of water were added, and after liquid separation extraction was conducted, the organic phase was charged into a large amount of hexane to permit reprecipitation. Filtration of the mixture followed by recovery and drying of the precipitate gave 26.2 g of the compound (A-6).

Example 1-7

Into a reaction container, 50 g of 4-cyanophenol and 500 g of dichloromethane were added and dissolution was allowed at room temperature in a nitrogen atmosphere. After cooling the mixture to 0° C. and then adding thereto 315 g of trifluoromethanesulfonic acid dropwise, the reaction was allowed for 24 hrs by warming to 30° C. The reaction solution was neutralized with a 1% by mass aqueous ammonium hydroxide solution, and the precipitate was recovered by filtration. A resulting precipitate was recrystallized in methyl ethyl ketone, and dried to give 36.0 g of a compound represented by the following formula (a-7) (hereinafter, may be also referred to as "compound (a-7)").

(a-7)

Into a reaction container, 20.0 g of the compound (a-7), 120 g of N,N-dimethylacetamide, and 25.5 g of potassium carbonate were added in a nitrogen atmosphere. Thereafter, the mixture was warmed to 50° C. and thereto was added 22.4 g of 4-fluorobenzonitrile, and a reaction was allowed at 120° C. for 8 hrs. To the reaction solution, 40 g of methyl isobutyl ketone, 40 g of tetrahydrofuran, and 240 g of water were added, and after liquid separation extraction was conducted, the organic phase was charged into a large amount of hexane to permit reprecipitation. Filtration of the mixture followed by recovery and drying of the precipitate gave 32.5 g of the compound (A-7).

Example 1-8

In a similar manner to Example 1-1 except that 52.0 g of propargyl bromide in Example 1-1 was changed to 52.8 g of allyl bromide, 27.8 g of the compound (A-8) was obtained.

Example 1-9

Into a reaction container, 20.0 g of the compound (a-1), 200 g of pyridine, and 44.6 g of acetic anhydride were added in a nitrogen atmosphere, and thereafter a reaction was allowed at 115° C. for 8 hrs. To the reaction solution, 40 g of methyl isobutyl ketone, 40 g of tetrahydrofuran, and 240 g of water were added, and after liquid separation extraction was conducted, the organic phase was charged into a large amount of hexane to permit reprecipitation. Filtration of the mixture followed by recovery and drying of the precipitate gave 30.0 g of the compound (A-9).

Example 1-10

In a similar manner to Example 1-1 except that 52.0 g of propargyl bromide in Example 1-1 was changed to 40.4 g of epichlorohydrin, 28.2 g of the compound (A-10) was obtained.

Synthesis Example 1-1

Into a reaction container, 250.0 g of m-cresol, 125.0 g of 37% by mass formalin, and 2 g of anhydrous oxalic acid were added in a nitrogen atmosphere, and a reaction was allowed at 100° C. for 3 hrs and at 180° C. for 1 hour. Thereafter, an unreacted monomer was eliminated under a reduced pressure to give a resin represented by the following formula (x-1). A weight average molecular weight (Mw) of a resin (x-1) thus obtained was determined to be 11,000 as a result of a measurement by gel permeation chromatography (detector: differential refractometer) with GPC columns available from Tosoh Corporation ("G2000HXL"×2; and "G3000HXL"×1) under analytical conditions involving a flow rate of 1.0 mL/min, an elution solvent of tetrahydrofuran, and a column temperature of 40° C., using monodispersed polystyrene as a standard.

(x-1)

Preparation of Composition for Resist Underlayer Film Formation

The compound (A), the solvent (B), the acid generating agent (C), and the crosslinking agent (D) used in preparation of the compositions for resist underlayer film formation are as presented below.

(A) Compound

Examples: the compounds (A-1) to (A-10) synthesized as described above

Comparative Example: the resin (x-1) synthesized as described above (B) Solvent

B-1: propylene glycol monomethyl ether acetate

B-2: ethyl lactate

B-3: cyclohexanone (C) Acid Generating Agent

C-1: bis(4-t-butylphenyl)iodonium nonafluoro-n-butane-sulfonate (a compound represented by the following formula (C-1))

(C-1)

(D) Crosslinking Agent

D-1: 1,3,4,6-tetrakis(methoxymethyl)glycoluril (a compound represented by the following formula (D-1))

(D-1)

Example 2-1

Ten parts by mass of (A-1) as the compound (A) were dissolved in 90 parts by mass of (B-1) as the solvent (B). A solution thus obtained was filtered through a membrane filter having a pore size of 0.1 μm to prepare a composition for resist underlayer film formation (J-1).

Examples 2-2 to 2-10 and Comparative Example 2-1

Compositions for resist underlayer film formation (J-2) to (J-10) and (CJ-1) were prepared by a similar operation to that of Example 2-1 except that for each component, the type and content shown in Table 1 were used. In Table 1, "-" indicates that a corresponding component was not used. The "proportion of hydrogen atoms contained (% by mass)" in Table 1 shows a value calculated.

absolute value of a numerical value determined according to $(X_1-X_0) \times 100/X_0$ was calculated and designated as a rate of change in film thickness (%). The resistance to organic solvents was evaluated to be: "A" (favorable) in a case in which the rate of change in film thickness was less than 1%; "B" (somewhat favorable) in a case in which the rate of change in film thickness was no less than 1% and less than 5%; and "C" (unfavorable) in a case in which the rate of change in film thickness was no less than 5%.

Flatness

Each of the compositions for resist underlayer film formation prepared as described above was applied by a spin-coating procedure using a spin coater ("CLEAN TRACK ACT-12" available from Tokyo Electron Limited),

TABLE 1

| | Composition for resist underlayer film formation | (A) Compound | | | (B) Solvent | | (C) Acid generating agent | | (D) Crosslinking agent | |
|---|---|---|---|---|---|---|---|---|---|---|
| | | Type | proportion of hydrogen atoms contained (% by mass) | content (parts by mass) | type | content (parts by mass) | type | content (parts by mass) | type | content (parts by mass) |
| Example 2-1 | J-1 | A-1 | 4.18 | 10 | B-1 | 90 | — | — | — | — |
| Example 2-2 | J-2 | A-2 | 4.30 | 10 | B-1 | 90 | — | — | — | — |
| Example 2-3 | J-3 | A-3 | 4.12 | 10 | B-3 | 90 | — | — | — | — |
| Example 2-4 | J-4 | A-4 | 4.41 | 10 | B-1 | 90 | — | — | — | — |
| Example 2-5 | J-5 | A-5 | 3.01 | 10 | B-2 | 90 | — | — | — | — |
| Example 2-6 | J-6 | A-6 | 0.89 | 10 | B-2 | 90 | — | — | — | — |
| Example 2-7 | J-7 | A-7 | 3.66 | 10 | B-3 | 90 | C-1 | 0.5 | D-1 | 3 |
| Example 2-8 | J-8 | A-8 | 6.32 | 10 | B-1 | 90 | — | — | — | — |
| Example 2-9 | J-9 | A-9 | 4.00 | 10 | B-1 | 90 | C-1 | 0.5 | D-1 | 3 |
| Example 2-10 | J-10 | A-10 | 4.00 | 10 | B-1 | 90 | C-1 | 0.5 | D-1 | 3 |
| Comparative Example 2-1 | CJ-1 | a-1 | 6.72 | 10 | B-1 | 90 | C-1 | 0.5 | D-1 | 3 |

Formation of Resist Underlayer Film

Examples 3-1 to 3-10 and Comparative Example 3-1

The composition for resist underlayer film formation prepared as described above was applied on an 8-inch silicon wafer (substrate) with a spin coater ("CLEAN TRACK ACT12" available from Tokyo Electron Limited) by way of a spin-coating procedure. Next, heating (baking) in an ambient air atmosphere at the heating temperature (° C.) for the heating time period (sec) shown in Table 2 below was followed by cooling at 23° C. for 60 sec to form a resist underlayer film having an average thickness of 200 nm. Accordingly, a resist underlayer film-attached substrate having been provided with the resist underlayer film thereon was obtained.

Evaluations

By using the compositions for resist underlayer film formation obtained and the resist underlayer film-attached substrates obtained, the following evaluations were each made according to the following procedures. The results of the evaluations are shown together in Table 2 below.

Resistance to Organic Solvents

Figure 1:
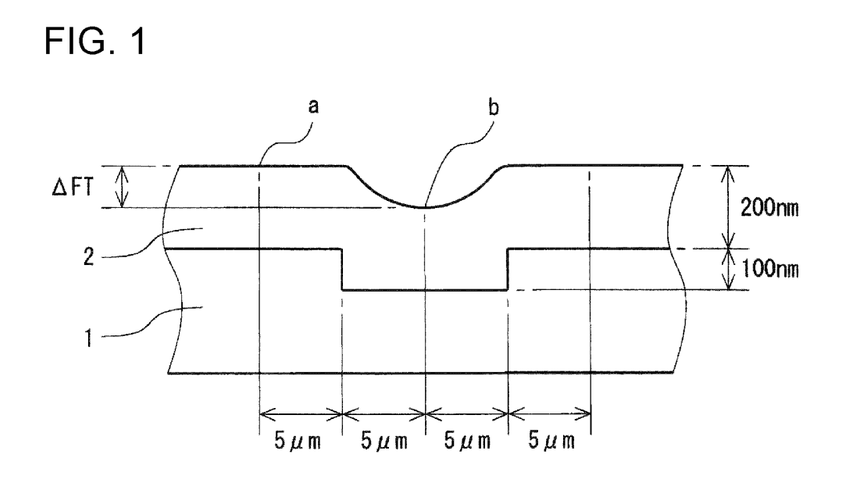
FIG. 1 is a schematic cross sectional view for illustrating an evaluation method of flatness.

After the resist underlayer film-attached substrate obtained as described above was immersed in cyclohexanone (at room temperature) for 1 min, compressed air was blown for 20 sec to dry the substrate. Average thicknesses of the film before and after the immersion were measured. The average thickness of the film before the immersion was designated as $X_0$ and the average thickness of the film after the immersion was designated as $X_1$, and an on a silicon substrate 1 provided with a trench pattern having a depth of 100 nm and a groove width of 10 μm formed thereon, as shown in FIG. 1. A rotational speed for the spin coating was the same as that in the case of forming the film having the average thickness of 200 nm in the "Film Formation" as above. Subsequently, by heating (baking) in an ambient air atmosphere at a heating temperature (° C.) for a heating time period (sec) shown in Table 2 below, a film 2 was formed having an average thickness of 200 nm at parts having no trench provided. Accordingly, a film-attached silicon substrate, the silicon substrate being covered by the film, was obtained.

A cross-sectional shape of the resist underlayer film-attached silicon substrate was observed by using a scanning electron microscope ("S-4800" available from Hitachi High-Technologies Corporation), and the difference (ΔFT) between a height at the center portion "b" of the trench pattern of the film and a height at a position "a" 5 μm away from the edge of the trench pattern, at which no trench pattern was provided, was defined as a marker of the flatness. The flatness was evaluated to be: "A" (favorable) in a case of ΔFT being less than 40 nm; "B" (somewhat favorable) in a case of ΔFT being no less than 40 nm and less than 60 nm; and "C" (unfavorable) in a case of ΔFT being no less than 60 nm. It is to be noted that the difference in heights shown in FIG. 1 is exaggerated.

Flexural Resistance

The composition for resist underlayer film formation prepared as described above was applied by a spin-coating procedure on a silicon substrate on which a thermally-oxidized film having an average thickness of 500 nm had been formed. A film-attached substrate, having been provided with the film thereon, having an average thickness of 200 nm was obtained by thereafter heating (baking) at 350° C. for 60 sec in an ambient air atmosphere. On the film-attached substrate thus obtained, a composition for silicon-containing film formation ("NFC SOG080" available from JSR Corporation) was applied by a spin-coating procedure and then heated (baked) at 200° C. for 60 sec in an ambient air atmosphere, followed by additional heating (baking) at 300° C. for 60 sec to form a silicon-containing film having an average thickness of 50 nm. Next, a resist composition for ArF ("AR1682J" available from JSR Corporation) was applied on the silicon-containing film by a spin-coating procedure and then heated (baked) at 130° C. for 60 sec in an ambient air atmosphere to form a resist film having an average thickness of 200 nm. Thereafter, the resist film was subjected to an exposure with an exposure dose altered through a 1:1 line-and-space mask pattern with a target size of 100 nm by using an ArF excimer laser lithography device available from Nikon Corporation (lens numerical aperture: 0.78; exposure wavelength: 193 nm), and then heated (baked) at 130° C. for 60 sec in an ambient air atmosphere. A development was carried out with a 2.38% by mass aqueous tetramethylammonium hydroxide (TMAH) solution at 25° C. for 1 min, followed by washing with water and drying. Accordingly, a line-and-space resist-patterned substrate with a pitch of 200 nm was obtained having a line width of the line pattern being from 30 nm to 100 nm.

Using the resist pattern as a mask, the silicon-containing film was etched with an etching apparatus ("TACTRAS" available from Tokyo Electron Limited) under a condition of $CF_4$=200 sccm, PRESS.=85 mT, HF RF (high-frequency power for plasma production)=500 W, LF RF (high-frequency power for bias)=0 W, DCS=−150 V, and RDC (proportion of gas center flow rate)=50% to give a substrate patterned on the silicon-containing film. Next, using the silicon-containing film pattern as a mask, the film was etched with the etching apparatus ("TACTRAS" available from Tokyo Electron Limited) under a condition of $O_2$=400 sccm, PRESS.=25 mT, HF RF (high-frequency power for plasma production)=400 W, LF RF (high-frequency power for bias)=0 W, DCS=0 V, and RDC (proportion of gas center flow rate)=50% to give the substrate patterned on the film. Using the film pattern as a mask, the thermally-oxidized film was etched with an etching apparatus ("TACTRAS" available from Tokyo Electron Limited) under a condition of $CF_4$=180 sccm, Ar=360 sccm, PRESS.=150 mT, HF RF (high-frequency power for plasma production)=1,000 W, LF RF (high-frequency power for bias)=1,000 W, DCS=−150 V, and RDC (proportion of gas center flow rate)=50%, for 60 sec.

Figure 2:
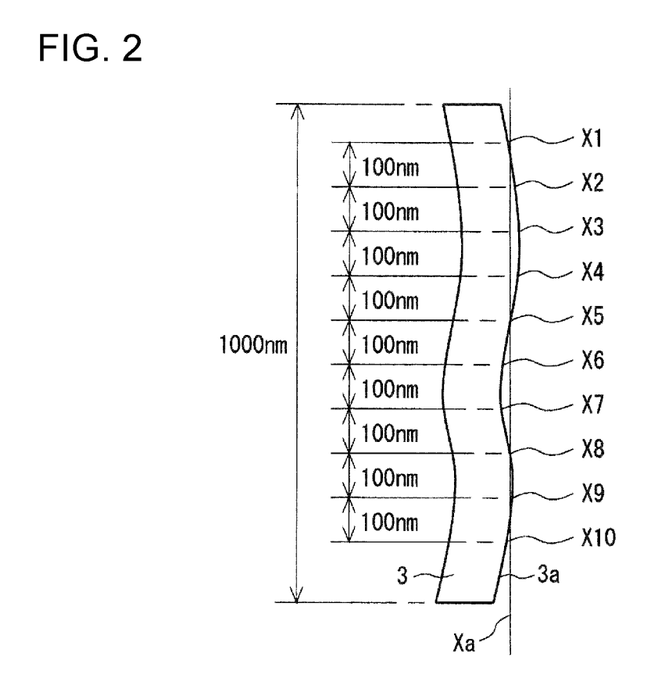
FIG. 2 is a schematic plan view for illustrating an evaluation method of flexural resistance.

Thereafter, a 250,000 times enlarged image of the configuration of the film pattern with each line width was obtained using a scanning electron microscope ("CG-4000" available from Hitachi High-Technologies Corporation), and image processing thereof was executed. Accordingly, as shown in FIG. 2, LER (line-edge roughness) was determined on a side lateral face 3a of a film pattern 3 (line pattern) with a length of 1,000 nm in the configuration thus observed, in terms of a 3 Sigma value derived by triplicating a standard deviation calculated from: positions Xn (n=1 to 10) in a line width direction measured at ten points with intervals of 100 nm; and a position Xa corresponding to an average of these positions in the line width direction. LER, indicating a degree of bending of the film pattern, increases as the line width of the film pattern decreases. On the basis of the line width of the film pattern that results in LER of 5.5 nm, the flexural resistance was evaluated to be: "A" (favorable) in a case in which this line width was less than 40.0 nm; "B" (somewhat favorable) in a case in which this line width was no less than 40.0 nm and less than 45.0 nm; and "C" ("unfavorable") in a case in which this line width was no less than 45.0 nm. It is to be noted that the manner of bending of the film pattern shown in FIG. 2 is exaggeratedly illustrated.

TABLE 2

| | Composition for resist underlayer film formation | Heating temperature/ heating time period in resist underlayer film-forming (° C./sec) | Solvent resistance | Flatness | Flexural resistance |
|---|---|---|---|---|---|
| Example 3-1 | J-1 | 350/60 | A | A | A |
| Example 3-2 | J-2 | 350/60 | A | A | A |
| Example 3-3 | J-3 | 350/60 | A | A | A |
| Example 3-4 | J-4 | 350/60 | A | A | A |
| Example 3-5 | J-5 | 350/60 | A | A | A |
| Example 3-6 | J-6 | 350/60 | A | A | A |
| Example 3-7 | J-7 | 350/60 | A | A | A |
| Example 3-8 | J-8 | 350/60 | A | A | B |
| Example 3-9 | J-9 | 350/60 | A | A | A |
| Example 3-10 | J-10 | 350/60 | A | A | B |
| Comparative Example 3-1 | CJ-1 | 350/60 | A | C | C |

As is revealed from the results shown in Table 2, the resist underlayer films formed from the compositions for resist underlayer film formation of the Examples were superior in the flatness and the flexural resistance of the pattern, with the resistance to organic solvents being maintained. To the contrary, the resist underlayer film formed from the composition for resist underlayer film formation of the Comparative Example was superior in the resistance to organic solvents; however the flatness and the flexural resistance of the pattern were inferior.

The composition for resist underlayer film formation of the embodiment of the present invention enables formation of a resist underlayer film that is superior in flatness and flexural resistance of a pattern, with resistance to organic solvents being maintained. The resist underlayer film of the embodiment of the present invention is superior in flatness and flexural resistance of a pattern, with resistance to organic solvents being maintained. The resist underlayer film-forming method of the embodiment of the present invention enables a resist underlayer film that is superior in flatness and flexural resistance of a pattern to be formed, with resistance to organic solvents being maintained. The patterned substrate-producing method of the embodiment of the present invention enables a favorable patterned substrate to be obtained by using such a superior resist underlayer film. The compound of the embodiment of the present invention can be suitably used as a component of the composition for resist underlayer film formation of the embodiment of the invention. Therefore, these can be suitably used for manufacture, etc., of semiconductor devices in which further progress of microfabrication is expected in the future.

Obviously, numerous modifications and variations of the present invention are possible in light of the above teachings. It is therefore to be understood that within the scope of the appended claims, the invention may be practiced otherwise than as specifically described herein.

What is claimed is:

1. A composition for resist underlayer film formation, comprising:
a compound represented by formula (1); and
a solvent, wherein, in the formula (1),
$Ar^1$ represents a 1,3,5-triazinetriyl group;
m is an integer of 3;
$Ar^2$ is a group bonding to a carbon atom of the 1,3,5-triazinetriyl group represented by $Ar^1$ and represents an aromatic carbocyclic group having 6 to 20 ring atoms and having a valency of (n+1);
n is an integer of 0 to 12,
wherein a plurality of $Ar^2$s are identical or different from each other, and a plurality of n's are identical or different from each other; and
$R^1$ represents a monovalent organic group having 1 to 20 carbon atoms, a hydroxy group, a halogen atom, or a nitro group,
wherein the number of $R^1$s in the compound is three or more,
wherein at least three $R^1$s each represent an organic group comprising at least one multiple bond or an organic group comprising an epoxy group, the at least one multiple bond being selected from the group consisting of: an ethylenic carbon-carbon double bond; a carbon-carbon triple bond; a carbon-nitrogen double bond; a carbon-nitrogen triple bond; and a carbon-oxygen double bond, and
wherein in a case in which $R^1$ is present in a plurality of number, a plurality of $R^1$s are identical or different from each other.

2. The composition according to claim 1, wherein $Ar^2$ in the formula (1) represents a group obtained from benzene by removing (n+1) hydrogen atoms bonding to a carbon atom of an aromatic carbon ring.

3. The composition according to claim 1, wherein the monovalent organic group having 1 to 20 carbon atoms represented by $R^1$ in the formula (1) is:
a monovalent hydrocarbon group having 1 to 20 carbon atoms;
a group in which a divalent hetero atom-containing group is inserted between two adjacent carbon atoms of a monovalent hydrocarbon group having 1 to 20 carbon atoms;
a group comprising a divalent hetero atom-containing group and a monovalent hydrocarbon group having 1 to 20 carbon atoms, wherein the divalent hetero atom-containing group is positioned between the monovalent hydrocarbon group and an atom constituting $Ar^2$;
a group obtained by substituting with a monovalent hetero atom-containing group, a part or all of hydrogen atoms included in a monovalent hydrocarbon group having 1 to 20 carbon atoms;
a group obtained by substituting with a monovalent hetero atom-containing group, a part or all of hydrogen atoms included in a group in which a divalent hetero atom-containing group is inserted between two adjacent carbon atoms of a monovalent hydrocarbon group having 1 to 20 carbon atoms;
a group obtained by substituting with a monovalent hetero atom-containing group, a part or all of hydrogen atoms included in a group comprising a divalent hetero atom-containing group and a monovalent hydrocarbon group having 1 to 20 carbon atoms, wherein the divalent hetero atom-containing group is positioned between the monovalent hydrocarbon group and an atom constituting $Ar^2$; or
a group comprising a divalent hetero atom-containing group and a monovalent hetero atom-containing group, wherein the divalent hetero atom-containing group is positioned between the monovalent hetero atom-containing group and an atom constituting $Ar^2$.

4. The composition according to claim 1, wherein the monovalent organic group having 1 to 20 carbon atoms represented by $R^1$ in the formula (1) is a group represented by formula (2):

wherein, in the formula (2), X represents a single bond or a divalent hetero atom-containing group; $R^{1'}$ represents a monovalent hydrocarbon group having 1 to 20 carbon atoms, a monovalent hetero atom-containing group, or a group obtained by substituting with a monovalent hetero atom-containing group, a part or all of hydrogen atoms included in a monovalent hydrocarbon group having 1 to 20 carbon atoms; and * denotes a bonding site to $Ar^2$.

5. The composition according to claim 1, further comprising at least one selected from the group consisting of an acid generating agent and a crosslinking agent.

6. The composition according to claim 1, wherein in the formula (1), n is an integer of 2 to 8.

7. The composition according to claim 1, wherein in the formula (1), n is an integer of 3 to 6.

8. The composition according to claim 1, wherein the at least one multiple bond is selected from the group consisting of: an ethylenic carbon-carbon double bond; a carbon-carbon triple bond; a carbon-nitrogen double bond; and a carbon-nitrogen triple bond.

9. The composition according to claim 1, wherein the at least one multiple bond is selected from the group consisting of: a carbon-carbon triple bond; and a carbon-nitrogen triple bond.

10. A resist underlayer film formed from the composition according to claim 1.

11. A resist underlayer film-forming method comprising:
applying the composition according to claim 1 directly or indirectly on one face side of a substrate to form a coating film; and
heating the coating film.

12. A patterned substrate-producing method comprising:
applying a composition for resist underlayer film formation comprising a compound represented by formula (1) and a solvent, directly or indirectly on an upper face side of a substrate to form a coating film;
heating the coating film to form a resist underlayer film;
forming a resist pattern on an upper face side of the resist underlayer film; and
etching the substrate using the resist pattern as a mask, wherein, in the formula (1),
$Ar^1$ represents a 1,3,5-triazinetriyl group;
m is an integer of 3;
$Ar^2$ is a group bonding to a carbon atom of the 1,3,5-triazinetriyl group represented by $Ar^1$ and represents an aromatic carbocyclic group having 6 to 20 ring atoms and having a valency of (n+1);

n is an integer of 0 to 12, wherein a plurality of $Ar^2$s are identical or different from each other, and a plurality of n's are identical or different from each other; and $R^1$ represents a monovalent organic group having 1 to 20 carbon atoms, a hydroxy group, a halogen atom, or a nitro group, wherein the number of $R^1$s in the compound is three or more, wherein at least three $R^1$s each represent an organic group comprising at least one multiple bond or an organic group comprising an epoxy group, the at least one multiple bond being selected from the group consisting of: an ethylenic carbon-carbon double bond; a carbon-carbon triple bond; a carbon-nitrogen double bond; a carbon-nitrogen triple bond; and a carbon-oxygen double bond, and wherein in a case in which $R^1$ is present in a plurality of number, a plurality of $R^1$s are identical or different from each other.

13. The patterned substrate-producing method according to claim 12, further comprising forming a silicon-containing film on the upper face side of the resist underlayer film before forming the resist pattern.

14. The patterned substrate-producing method according to claim 12, wherein $Ar^2$ in the formula (1) represents a group obtained from benzene by removing (n+1) hydrogen atoms bonding to a carbon atom of an aromatic carbon ring.

15. The patterned substrate-producing method according to claim 12, wherein the monovalent organic group having 1 to 20 carbon atoms represented by $R^1$ in the formula (1) is:

a monovalent hydrocarbon group having 1 to 20 carbon atoms;

a group in which a divalent hetero atom-containing group is inserted between two adjacent carbon atoms of a monovalent hydrocarbon group having 1 to 20 carbon atoms;

a group comprising a divalent hetero atom-containing group and a monovalent hydrocarbon group having 1 to 20 carbon atoms, wherein the divalent hetero atom-containing group is positioned between the monovalent hydrocarbon group and an atom constituting $Ar^2$;

a group obtained by substituting with a monovalent hetero atom-containing group, a part or all of hydrogen atoms included in a monovalent hydrocarbon group having 1 to 20 carbon atoms;

a group obtained by substituting with a monovalent hetero atom-containing group, a part or all of hydrogen atoms included in a group in which a divalent hetero atom-containing group is inserted between two adjacent carbon atoms of a monovalent hydrocarbon group having 1 to 20 carbon atoms;

a group obtained by substituting with a monovalent hetero atom-containing group, a part or all of hydrogen atoms included in a group comprising a divalent hetero atom-containing group and a monovalent hydrocarbon group having 1 to 20 carbon atoms, wherein the divalent hetero atom-containing group is positioned between the monovalent hydrocarbon group and an atom constituting $Ar^2$; or a group comprising a divalent hetero atom-containing group and a monovalent hetero atom-containing group, wherein the divalent hetero atom-containing group is positioned between the monovalent hetero atom-containing group and an atom constituting $Ar^2$.

16. The patterned substrate-producing method according to claim 12, wherein the monovalent organic group having 1 to 20 carbon atoms represented by $R^1$ in the formula (1) is a group represented by formula (2):

$$*-X-R^{1'} \quad (2)$$

wherein, in the formula (2), X represents a single bond or a divalent hetero atom-containing group; $R^{1'}$ represents a monovalent hydrocarbon group having 1 to 20 carbon atoms, a monovalent hetero atom-containing group, or a group obtained by substituting with a monovalent hetero atom-containing group, a part or all of hydrogen atoms included in a monovalent hydrocarbon group having 1 to 20 carbon atoms; and * denotes a bonding site to $Ar^2$.

17. The patterned substrate-producing method according to claim 12, wherein in the formula (1), n is an integer of 2 to 8.

18. The patterned substrate-producing method according to claim 12, wherein in the formula (1), n is an integer of 3 to 6.

19. The patterned substrate-producing method according to claim 12, wherein the at least one multiple bond is selected from the group consisting of: an ethylenic carbon-carbon double bond; a carbon-carbon triple bond; a carbon-nitrogen double bond; and a carbon-nitrogen triple bond.

20. A compound represented by formula (1'):

$$Ar^1\!\!-\!\!(Ar^2\!\!-\!\!(R^1)_n)_m \qquad (1')$$

wherein, in the formula (1'), $Ar^1$ represents a 1,3,5-triazinetriyl group;

m is an integer of 3;

$Ar^2$ is a group bonding to a carbon atom of the 1,3,5-triazinetriyl group represented by $Ar^1$ and represents an aromatic carbocyclic group having 6 to 20 ring atoms and having a valency of (n+1);

n is an integer of 0 to 12, wherein a plurality of $Ar^2$s are identical or different from each other, and a plurality of n's are identical or different from each other; and $R^1$ represents a monovalent organic group having 1 to 20 carbon atoms, a hydroxy group, a halogen atom, or a nitro group, wherein the number of $R^1$s in the compound is three or more, wherein at least three 1es each represent an organic group comprising at least one multiple bond or an organic group comprising an epoxy group, the at least one multiple bond being selected from the group consisting of: an ethylenic carbon-carbon double bond; a carbon-carbon triple bond; a carbon-nitrogen double bond; a carbon-nitrogen triple bond; and a carbon-oxygen double bond, and wherein in a case in which $R^1$ is present in a plurality of number, a plurality of $R^1$s are identical or different from each other.

* * * * *